(12) United States Patent
Duan et al.

(10) Patent No.: US 11,512,006 B2
(45) Date of Patent: Nov. 29, 2022

(54) METHOD FOR SIMULTANEOUSLY PREPARING IRON OXIDE RED PIGMENT AND AROMATIC AMINE

(71) Applicant: HEBEI CAIKE CHEMICAL CO., LTD., Cangzhou (CN)

(72) Inventors: Weidong Duan, Cangzhou (CN); Guofu Zhang, Cangzhou (CN); Yu Wei, Cangzhou (CN)

(73) Assignee: HEBEI CAIKE CHEMICAL CO., LTD., Cangzhou (CN)

( * ) Notice: Subject to any disclaimer, the term of this patent is extended or adjusted under 35 U.S.C. 154(b) by 0 days.

(21) Appl. No.: 17/603,005

(22) PCT Filed: Nov. 20, 2020

(86) PCT No.: PCT/CN2020/130584
§ 371 (c)(1),
(2) Date: Oct. 12, 2021

(87) PCT Pub. No.: WO2021/129268
PCT Pub. Date: Jul. 1, 2021

(65) Prior Publication Data
US 2022/0177323 A1    Jun. 9, 2022

(30) Foreign Application Priority Data
Dec. 25, 2019    (CN) .......................... 201911351348.4

(51) Int. Cl.
*C01G 49/06*    (2006.01)
*C09C 1/24*    (2006.01)
(Continued)

(52) U.S. Cl.
CPC ............ *C01G 49/06* (2013.01); *C07C 209/36* (2013.01)

(58) Field of Classification Search
CPC ......... C01G 49/06; C09C 1/24; C07C 303/22; C07C 209/36
See application file for complete search history.

(56) References Cited

U.S. PATENT DOCUMENTS 1,793,942 A    2/1931    Laux
4,139,398 A *  2/1979    Pellizzon .................. C09C 1/24
                                                           564/417
(Continued)

FOREIGN PATENT DOCUMENTS

CN    1458134 A      11/2003
CN    101037393 A     9/2007
(Continued)

OTHER PUBLICATIONS

He Li-Fang, et al., Current Situation and Outlook of Aromatic Amine Synthesis, Yunnan Metallurgy, 2005, vol. 34 No. 3.

*Primary Examiner* — Matthew E. Hoban
(74) *Attorney, Agent, or Firm* — Bayramoglu Law Offices LLC

(57) ABSTRACT

A method for simultaneously preparing an iron oxide red pigment and an aromatic amine is provided. In the method, an aromatic nitro compound and ferrous iron are first used to prepare an iron oxide red seed crystal under the action of a catalyst, and then iron powder is used to reduce the aromatic nitro compound and generate iron oxide in situ which grows into iron oxide red with pigment performance on the seed crystal. The method provides a clean and economical way for the reduction of an aromatic nitro compound (especially those in which there are other easily-reduced substituents on an aromatic ring) to prepare an aromatic amine.

6 Claims, 1 Drawing Sheet

(51) Int. Cl.
*C07C 303/22* (2006.01)
*C07C 209/36* (2006.01)

(56) References Cited

U.S. PATENT DOCUMENTS

| | | | |
|---|---|---|---|
| 4,142,915 A | | 3/1979 | Pellizzon et al. |
| 4,153,472 A | * | 5/1979 | Pellizzon ............... C01G 49/06 564/417 |
| 4,358,431 A | * | 11/1982 | Brunn .................... C01G 49/06 |

FOREIGN PATENT DOCUMENTS

| | | |
|---|---|---|
| CN | 101376634 A | 3/2009 |
| CN | 103193690 A | 7/2013 |
| CN | 105085332 A | 11/2015 |
| CN | 109761860 A | 5/2019 |
| CN | 111233045 A | 6/2020 |

* cited by examiner

METHOD FOR SIMULTANEOUSLY PREPARING IRON OXIDE RED PIGMENT AND AROMATIC AMINE

CROSS REFERENCE TO THE RELATED APPLICATIONS

This application is the national stage entry of International Application No. PCT/CN2020/130584, filed on Nov. 20, 2020, which is based upon and claims priority to Chinese Patent Application No. 201911351348.4, filed on Dec. 25, 2019, the entire contents of which are incorporated herein by reference.

TECHNICAL FIELD

The present disclosure relates to the technical field of fine chemicals, and in particular to a method for simultaneously preparing an iron oxide red pigment and an aromatic amine.

BACKGROUND

Aromatic amines are important chemical intermediates and can be used to synthesize fine chemicals such as dyes, medicines, and pesticides. Aromatic amines are typically prepared by reducing aromatic nitro compounds, and specifically, the preparation methods thereof mainly include catalytic hydrogenation, iron powder/acid reduction, alkali sulfide reduction, and hydrogen transfer reduction. These methods each have advantages as well as disadvantages. The catalytic hydrogenation is the cleanest and simplest reduction method, but for molecules containing hydrogenation-sensitive functional groups, such as halogen, double bond, and triple bond, the catalytic hydrogenation possesses a poor reduction selectivity. The alkali sulfide reduction shows, to a certain extent, selectivity for the reduction of polynitro, but the waste water produced will pollute the environment. Hydrogen transfer reagents commonly used in the hydrogen transfer reduction include hydrazine hydrate, sodium borohydride, formic acid and a salt thereof, hypophosphorous acid, isopropanol, and the like. The hydrogen transfer reduction is characterized by mild reaction conditions and high selectivity, but the hydrogen transfer reagents are not superior in industrial production due to their expensive price. The iron powder reduction is basically applicable to the reduction of all nitro compounds. The Chinese Patent No. CN101037393A discloses a coupling process of iron powder reduction and hydrazine hydrate reduction for preparing an aromatic diamine by reducing an aromatic nitro compound, including: adding a reduced iron powder, an electrolyte, a solvent, and a nitro compound to a reactor and reacting for a specified time period at about 100° C.; then adding a catalyst to the reactor and dropwise adding hydrazine hydrate; and after the reaction is completed, filtering a resulting reaction solution, and distilling off the solvent to obtain a solid product. The Chinese Patent No. CN101376634A discloses a method for producing o-chloroaniline by iron powder reduction, including: adding o-nitrochlorobenzene, water, hydrochloric acid, and iron powder to a reactor for a reduction reaction at 90° C. to 100° C., and performing rake vacuum drying on a resulting reaction solution to separate out iron sludge. However, the treatment of solid waste is not described. The U.S. Pat. No. 1,793,942 discloses an aniline method (Laux process), including: treating or calcinating a by-product of iron oxide to obtain ferrous oxide black pigments and iron oxide red pigments, but this method cannot directly obtain the high-quality yellow-red phase iron oxide red pigment that is in great demand on the market. The Chinese Patent No. ZL201510484541.0 and the U.S. Pat. No. 4,142,915 both disclose the direct reduction of an aromatic nitro compound into an aromatic amine at a constant pH under the coexistence of iron oxide and ferrous iron, where ferrous iron is oxidized to produce iron oxide red or iron oxide yellow. However, this method consumes a large number of alkali, a salt-containing mother liquid needs to be desalted, and there is no cost advantage.

SUMMARY

A technical problem to be solved by the present disclosure is to provide a method for simultaneously preparing an iron oxide red pigment and an aromatic amine in view of the above-mentioned technical deficiencies. In the method, an aromatic nitro compound and ferrous iron are first used to prepare an iron oxide red seed crystal under the action of a catalyst, and then iron powder is used to reduce the aromatic nitro compound and generate iron oxide in situ which grows into iron oxide red with pigment performance on the seed crystal. The method provides a clean and economical way for the reduction of an aromatic nitro compound (especially those in which there are other easily-reduced substituents on an aromatic ring) to prepare an aromatic amine.

To solve the above technical problem, the present disclosure adopts the following technical solution, including the following steps:

step 1. adding a specified amount of water to an open reactor provided with a stirrer, adding a small amount of a catalyst, and heating a solution in the reactor to 85° C. to 90° C.; simultaneously adding a ferrous salt solution and an aromatic nitro compound solution dropwise to the reactor; and after the dropwise addition of the ferrous salt solution is completed, stopping the dropwise addition of the aromatic nitro compound solution, and using a liquid caustic soda to keep a pH of a solution in the reactor constant, where the aromatic nitro compound is reduced by ferrous ions to produce an aromatic amine and a $\alpha$-$Fe_2O_3$ crystal nucleus;

step 2. when the pH of the solution in the reactor decreases to 3.5 to 4.0 with the progress of a reaction, adding a same amount of iron powder to the reactor three times; adding the aromatic nitro compound solution left from the reaction in step 1 dropwise, during which a temperature of a solution in the reactor is kept at 85° C. to 88° C.; and after the dropwise addition of the aromatic nitro compound solution is completed, further keeping the reactor at the temperature for a specified time period to produce a mixture of iron oxide red and an aromatic amine; and step 3. separating and post-treating the iron oxide red and the aromatic amine obtained in step 2 by conventional methods to obtain the iron oxide red pigment and the aromatic amine.

As a further optimization of the technical solution, the catalyst used in step 1 may be $\alpha$-$Fe_2O_3$ with a particle size of less than 100 nm or newly-prepared amorphous $\delta$-FeOOH.

As a further optimization of the technical solution, the ferrous salt used in step 1 may be any one or a mixture of two from the group consisting of ferrous sulfate and ferrous chloride.

As a further optimization of the technical solution, a mass of the catalyst added in step 1 may be 0.1% to 1.0% of a mass of an iron oxide solid produced.

As a further optimization of the technical solution, in step 1, a molar ratio of ferrous iron to nitro in aromatic nitro compound molecules may be 6:1, and a consumption of the ferrous iron may be 25% to 30% of a theoretical consumption.

As a further optimization of the technical solution, in step 1, the liquid caustic soda may be used to keep the pH at 3.8 to 4.1.

As a further optimization of the technical solution, in step 2, when the pH of the solution in the reactor decreases to 3.5 to 3.8, the iron powder may be added for the first time, and after the iron powder reacts for 10 min, the aromatic nitro compound solution left from the reaction in step 1 may be added dropwise.

As a further optimization of the technical solution, in step 2, the dropwise addition of the aromatic nitro compound solution left from the reaction in step 1 may last for 210 min, and at 70 min and 140 min of the dropwise addition of the aromatic nitro compound solution, the iron powder may be added to the reactor for a second time and a third time, respectively.

As a further optimization of the technical solution, in step 2, the iron powder may have a mesh size of 80 to 200 mesh.

As a further optimization of the technical solution, in step 2, after the dropwise addition of the aromatic nitro compound solution is completed, the reactor may be further kept at the temperature for 40 min to 50 min.

Compared with the prior art, the present disclosure has the following advantages: 1. The present disclosure uses a ferrous salt to prepare a $\alpha$-$Fe_2O_3$ crystal nucleus under oxygen-free conditions, where added Fe(II) is converted into Fe(III) through the fast electron transfer between Fe(II) and an iron oxide interface structure Fe(III), the Fe(III) is hydrolyzed to form amorphous metastable $\delta$-FeOOH in situ, and the $\alpha$-$Fe_2O_3$ nucleus is formed from the $\delta$-FeOOH through phase transformation. Aromatic nitro can be reduced into aromatic amino by acquiring an electron of nascent Fe(II) on a surface of the structural iron oxide (the nascent Fe(II) has strong reducibility, and Fe(II) in the solution cannot be oxidized by the aromatic nitro compound). 2. In the preparation process of the $\alpha$-$Fe_2O_3$ crystal nucleus of the present disclosure, a liquid caustic soda is reasonably added to the reduction reactor to control a pH in the reduction reactor at 3.8 to 4.1, thereby ensuring the rapid hydrolysis of Fe(III) ions. 3. The method for preparing an aromatic amino compound and a pigment-grade iron oxide red by reducing an aromatic nitro compound provided by the present disclosure involves a simple production process and short reaction time, can be used for continuous production, has high operational safety and high reduction selectivity, and leads to a product with high quality and an aromatic amine content of more than 97%. 4. The co-produced iron oxide red pigment has prominent performance and can be directly sold as a commodity, which solves the problem that aromatic amine-containing iron sludge heavily pollutes the environment. The present disclosure provides a clean and economical method to prepare an aromatic amine through selective reduction of especially aromatic nitro compounds in which there are other easily-reduced substituents such as halogen, carbonyl, cyano, alkenyl, and alkynyl on an aromatic ring, and has excellent economic and social benefits.

The aromatic nitro compound in the present disclosure has a general chemical formula of $R_1$-Aryl($R_2$)—$NO_2$.

In the formula, Aryl is an aromatic group, $R_1$ and $R_2$ are two identical or different electron-withdrawing groups or electron-donating groups, and at least one of $R_1$ and $R_2$ is a group with an unsaturated bond;

the aromatic group may preferably be phenyl or naphthyl; and the above $R_1$ and $R_2$ may be each selected from the group consisting of $C_{1-6}$ alkyl, $C_{1-6}$ alkoxy, $C_{1-6}$ alkenyl, $C_{1-6}$ alkynyl, cyano, halogen, sulfonyl, formyl, and $C_{1-6}$ ketonic carbonyl, and $C_{1-6}$ acyl.

DETAILED DESCRIPTION OF THE EMBODIMENTS

Figure 1:
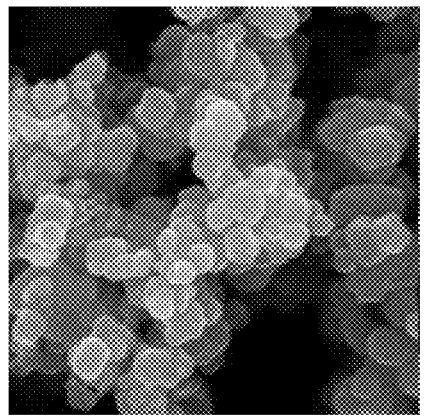
FIG. 1 is an electron micrograph for Example 1 of the method for simultaneously preparing an iron oxide red pigment and an aromatic amine.
Figure 2:
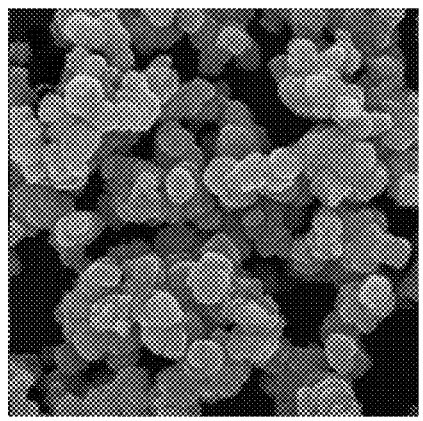
FIG. 2 is an electron micrograph for Example 2 of the method for simultaneously preparing an iron oxide red pigment and an aromatic amine.
Figure 3:
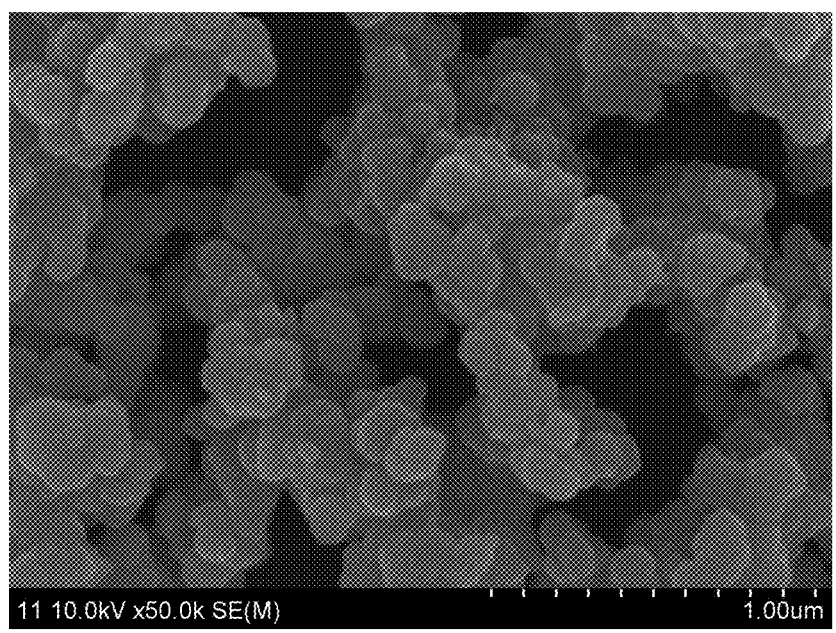
FIG. 3 is an electron micrograph for Example 3 of the method for simultaneously preparing an iron oxide red pigment and an aromatic amine.

To make the objectives, technical solutions, and advantages of the present disclosure clearer, the present disclosure is further described in detail below with reference to specific implementations. However, it should be understood that the description is exemplary and is not intended to limit the scope of the present disclosure. In addition, in the following description, descriptions of conventional structures and technologies are omitted to avoid unnecessarily confusing the concepts of the present disclosure.

Example 1

500 mm of bottom water was added to a stirrer-equipped reduction reactor with a diameter of 3,000 mm and a height of 3,600 mm, and then the reactor was heated to 80° C. to 85° C. 2,800 kg of solid $FeSO_4.7H_2O$ was added to the water, and a resulting mixture was heated to about 70° C. until the solid was completely dissolved. A resulting solution was diluted to a volume of 3.76 m$^3$. 842 Kg of 4,4'-dinitrostilbene-2,2'-disulfonic acid (DNS) was added to water, a resulting mixture was heated to 95° C. to make the DNS completely dissolved, and a resulting solution was diluted to a volume of 3.1 m$^3$. The DNS solution and a ferrous sulfate solution were simultaneously added to the reactor at a temperature controlled at 85° C. to 87° C. for a time controlled at about 50 min, and a pH of a reaction system was controlled at 4 to 4.1 using a liquid caustic soda. After the addition of the ferrous sulfate solution was completed, iron powder (80 mesh) was added for the first time; after the iron powder reacted for 10 min, the remaining DNS was added at a temperature controlled at 87° C. to 88° C. for a time controlled at 210 min, during which the remaining iron powder was added for a second time and a third time at 70 min and 140 min, respectively; and after the addition of the DNS was completed, the reactor was further kept at the temperature for 40 min, and then a reaction solution was discharged. The reaction solution was subjected to plate and frame filtration, and a resulting filter cake was washed and dried to obtain an iron oxide red powder, which was quasi-spherical particles with a particle size of 150 nm to 180 nm and had the following L*a*b* color standard compared with German BAYFERROX inorganic pigment iron oxide red 130 M: L*=45.48, a*=26.51, b*=17.1, and tinting strength: 95%. A filtrate was acidified to obtain a DSD acid, with a purity of 97.36%, an amino value of 43.18, a color strength of 5.0, and class I dying lines.

Example 2

500 mm of bottom water was added to a stirrer-equipped reduction reactor with a diameter of 3,000 mm and a height of 3,600 mm, and then the reactor was heated to 80° C. to 85° C. 3.41 m³ of a ferrous chloride solution with a concentration of 2.8 mol/L was added. 842 Kg of DNS was added to water, a resulting mixture was heated to 95° C. to make the DNS completely dissolved, and a resulting solution was diluted to a volume of 3.1 m³. The DNS solution and a ferrous chloride solution were simultaneously added to the reactor at a temperature controlled at 85° C. to 87° C. for a time controlled at about 50 min, and a pH of a reaction system was controlled at 4 to 4.1 using a liquid caustic soda. After the addition of the ferrous chloride solution was completed, iron powder (80 mesh) was added for the first time; after the iron powder reacted for 10 min, the remaining DNS was added dropwise at a temperature controlled at 87° C. to 88° C. for a time controlled at 210 min, during which the remaining iron powder was added for a second time and a third time at 70 min and 140 min, respectively; and after the addition of the DNS was completed, the reactor was further kept at the temperature for 50 min, and then a reaction solution was discharged. The reaction solution was subjected to plate and frame filtration, and a resulting filter cake was washed and dried to obtain an iron oxide red powder, which was quasi-spherical particles with a particle size of 160 nm to 190 nm and had the following L*a*b* color standard compared with German BAYFERROX inorganic pigment iron oxide red 130 M: L*=46.23, a*=27.14, b*=16.2, and tinting strength: 99%. A filtrate was acidified to obtain a DSD acid, with a purity of 97.51%, an amino value of 42.21, a color strength of 5.0, and class I dying lines.

Example 3

500 mm of bottom water was added to a stirrer-equipped reduction reactor with a diameter of 3,000 mm and a height of 3,600 mm, and then the reactor was heated to 80° C. to 85° C. 2,800 kg of FeSO₄·7H₂O was added to the water, and a resulting mixture was heated to about 70° C. until the solid was completely dissolved. A resulting solution was diluted to a volume of 3.76 m³. 842 Kg of DNS was added to water, a resulting mixture was heated to 95° C. to make the DNS completely dissolved, and a resulting solution was diluted to a volume of 3.1 m³. The DNS solution and a ferrous sulfate solution were simultaneously added to the reactor at a temperature controlled at 85° C. to 87° C. for a time controlled at about 50 min, and a pH of a reaction system was controlled at 4 to 4.1 using a liquid caustic soda. After the addition of the ferrous sulfate solution was completed, iron powder (200 mesh) was added for the first time; after the iron powder reacted for 10 min, the remaining DNS was added at a temperature controlled at 87° C. to 88° C. for a time controlled at 210 min, during which the remaining iron powder was added for a second time and a third time at 70 min and 140 min, respectively; and after the addition of the DNS was completed, the reactor was further kept at the temperature for 30 min, and then a reaction solution was discharged. The reaction solution was subjected to plate and frame filtration, and a resulting filter cake was washed and dried to obtain an iron oxide red powder, which was quasi-spherical particles with a particle size of 170 nm to 200 nm and had the following L*a*b* color standard compared with German BAYFERROX inorganic pigment iron oxide red 130 M: L*=45.12, a*=26.34, b*=16.36, and tinting strength: 96%. A filtrate was acidified to obtain a DSD acid, with a purity of 97.53%, an amino value of 42.15, a color strength of 5.0, and class I dying lines.

The preparation of the α-Fe₂O₃ crystal nucleus in Examples 1 to 3 of the present disclosure involves the following chemical reaction equations:

$$Fe(II) + Fe(III) \rightarrow Fe(III) + \equiv Fe(II) \qquad (I)$$

$$Fe(III) \rightarrow \delta\text{-FeOOH} + H^+ \qquad (II)$$

$$\delta\text{-FeOOH} + H_2O \rightarrow \alpha\text{-Fe}_2O_3 + H^+ \qquad (III)$$

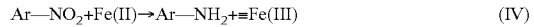

$$Ar\text{—}NO_2 + Fe(II) \rightarrow Ar\text{—}NH_2 + \equiv Fe(III) \qquad (IV)$$

total reaction:

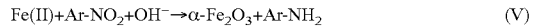

$$Fe(II) + Ar\text{-}NO_2 + OH^- \rightarrow \alpha\text{-Fe}_2O_3 + Ar\text{-}NH_2 \qquad (V)$$

Fe(III) and ≡Fe(III) involved in the present disclosure represent trivalent iron ion in a solution and trivalent iron in a surface structure of iron oxide, respectively;

Fe(II) and ≡Fe(II) involved in the present disclosure represent divalent iron ion in a solution and divalent iron in a surface structure of iron oxide, respectively; and ArNO₂ and ArNH₂ represent an aromatic nitro compound and an aromatic amine, respectively.

It should be understood that the above-mentioned specific implementations of the present disclosure are only used to exemplarily illustrate or explain the principle of the present disclosure, and do not constitute a limitation to the present disclosure. Any modifications, equivalent substitutions, and improvements made without departing from the spirit and scope of the present disclosure should be included in the protection scope of the present disclosure. In addition, the appended claims of the present disclosure are intended to cover all changes and modifications that fall within the scope and boundary of the appended claims or equivalent forms of such scope and boundary.

What is claimed is:

1. A method for simultaneously preparing an iron oxide red pigment and an aromatic amine, comprising the following steps:

step (1):

adding a specified amount of water to an open reactor provided with a stirrer, adding a catalyst to the open reactor to obtain a first solution, wherein a mass of the catalyst is 0.1% to 1.0% of a mass of the iron oxide red pigment produced, heating the first solution to 85° C. to 90° C. and simultaneously adding a solution of a ferrous salt and a solution of an aromatic nitro compound dropwise to the first solution, wherein a dropping rate of the solution of the ferrous salt is larger than a dropping rate of the solution of the aromatic nitro compound so that the solution of the aromatic nitro compound is left when the solution of the ferrous salt is completely consumed;

after finishing adding the solution of the ferrous salt, stopping adding the solution of the aromatic nitro compound to obtain a second solution, and using a caustic soda solution to tune a pH of the second solution to be 3.8-4.1, wherein the aromatic nitro compound is reduced by ferrous ions to produce an aromatic amine and an α-Fe₂O₃ crystal nucleus step (2):

adding a first amount of an iron powder to the second solution when the pH of the second solution decreases to 3.5 to 3.8;

after 10 min, adding dropwise the solution of the aromatic nitro compound left in the step (1) in a duration of 210 min to obtain a third solution, wherein a second amount of the iron powder is added at 70 minutes, and a third amount of the iron powder is added at 140 minutes; a temperature of the duration is kept from 85° C. to 88° C.; and after finishing adding the solution of the aromatic nitro compound keeping the third solution at the temperature for a period of time to produce a mixture of the iron oxide red pigment and the aromatic amine;

step (3):

filtering the mixture to obtain the iron oxide red pigment and a filtrate; and acidifying the filtrate to obtain the aromatic amine.

2. The method for simultaneously preparing the iron oxide red pigment and the aromatic amine according to claim 1, wherein the catalyst used in the step (1) is α-$Fe_2O_3$ with a particle size of less than 100 nm or in-situ amorphous δ-FeOOH.

3. The method for simultaneously preparing the iron oxide red pigment and the aromatic amine according to claim 1, wherein the ferrous salt is any one or a mixture of two from the group consisting of ferrous sulfate and ferrous chloride.

4. The method for simultaneously preparing the iron oxide red pigment and the aromatic amine according to claim 1, wherein in the step (2), the iron powder has a mesh size of 80 mesh to 100 mesh.

5. The method for simultaneously preparing the iron oxide red pigment and the aromatic amine according to claim 1, wherein in the step (2), the period of time is from 40 min to 50 min.

6. The method for simultaneously preparing the iron oxide red pigment and the aromatic amine according to claim 1, the first amount of the iron powder, the second amount of the iron powder, and the third amount of the iron powder are the same.

* * * * *